United States Patent [19]

Sawaya

[11] Patent Number: 5,394,982

[45] Date of Patent: Mar. 7, 1995

[54] CONTAINER FOR USE WITH MEDICAL INSTRUMENTS

[75] Inventor: Frederick J. Sawaya, West Bloomfield, Mich.

[73] Assignee: Specialized Health Products, Inc., Bountiful, Utah

[21] Appl. No.: 81,745

[22] Filed: Jun. 22, 1993

[51] Int. Cl.[6] .................... B65D 85/20; B65D 5/66
[52] U.S. Cl. .................... 206/366; 206/370; 229/125.37; 229/154
[58] Field of Search .............. 206/365, 366, 370, 438; 229/125.37, 125.39, 125.41, 128, 148-154

[56] References Cited

U.S. PATENT DOCUMENTS

| | | | |
|---|---|---|---|
| 930,113 | 8/1909 | Adams | 229/125.37 |
| 1,121,426 | 12/1914 | Walter | 229/154 |
| 1,697,359 | 1/1929 | Huffman | 229/125.39 |
| 1,820,804 | 8/1931 | Huffman | 229/125.39 |
| 2,226,215 | 12/1940 | Borah | 229/125.37 |
| 2,338,315 | 1/1944 | Borah | 229/125.37 |
| 3,496,536 | 2/1970 | Henry | 206/370 |
| 4,969,554 | 11/1990 | Sawaya | 206/370 |

*Primary Examiner*—Jimmy G. Foster
*Attorney, Agent, or Firm*—Paul S. Evans; Gale H. Thorne

[57] ABSTRACT

The container is optionally useful for transport of new sharp medical instruments, and for disposal of used sharp medical instruments. The container includes a pair of top flaps, a first of which pivots relative to the other. The second flap is selectively fixed to the body of the container to limit the opening to the interior of the body when the container is to be utilized for disposal of used sharp medical instruments. The second flap is typically not secured during transport such that it may be moved to provide a relatively large area or opening for insertion or removal of the new medical instruments. Several embodiments of the invention provide closure tabs at the ends of the second flap which are engageable with closure elements carried by the end walls of the container body to fix the second flap and to permit only a restricted opening into the interior of the container for the insertion of used sharp medical instruments.

9 Claims, 2 Drawing Sheets

CONTAINER FOR USE WITH MEDICAL INSTRUMENTS

BACKGROUND OF THE INVENTION

This application relates to a container for use with medical instruments and more particularly relates to a container which can be used to transport new sharp medical instruments to a place of use at a hospital or clinic and, after use of the sharp medical instruments the container may be used to dispose of the soiled or used medical instruments.

Prior art containers have been designed to facilitate the disposal of used sharp medical instruments such as scalpels, hypodermic syringes and needles or other biohazards. Such used sharp medical instruments may be contaminated by body fluids of the patient or for other reasons may require sanitary disposal. One such disposal device is a container which is useful for the disposal of sharp medical instruments such as needles or syringes as is disclosed and claimed in my U.S. Pat. No. 4,969,554, issued Nov. 13, 1990.

While the prior art containers have beneficial characteristics, it is desirable to improve the ability to transport the sharp medical instruments when new and associate the used sharps or biohazards with the disposal containers. In the prior art, new sharp medical instruments are typically transported in one container and then must be associated with a disposable container after the sharp instruments are used. The purposes of the prior art container disclosed in my U.S. Pat. No. 4,969,554 is to reduce any excess carrying of soiled instruments by medical personnel. Since the transport and disposal containers are not associated, some carrying is required with the prior art.

SUMMARY OF THE INVENTION

In a disclosed embodiment of the present invention, a single container may be utilized both for transport of the new sharp medical instruments, and also for disposal of the used sharp medical instruments. It should be understood, however, that the new sharp medical instruments may be separately packaged and the containers disclosed with the present invention used entirely to dispose of soiled sharp medical instruments as taught by my U.S. Pat. No. 4,969,554.

In a disclosed embodiment, a container is provided with a top panel having a pair of flaps which cooperate together to permit entrance into the interior of the container. In one position, the flaps may be completely opened to define a relatively large opening for the insertion of new sharp medical instruments into the interior of the container. Thereafter, the flaps are closed and the container with the new instruments therein is shipped to a hospital, doctors office or clinic for use. The medical personnel opens the top covers or flaps of the container to permit the new sharp medical instruments to be removed therefrom unrestrictedly. After the instruments have been removed from the interior of the container, the covers or flaps are permanently fixed in a closed position to define a restricted opening between the two top flaps or covers which extend laterally inwardly over the container space. An end of a first top flap or cover is received underneath the second top flap or cover. The first flap pivots relative to the body of the container such that one may place a used sharp medical instrument on the first flap, pivot it downwardly and allow that used sharp medical instrument to fall into the container space. The restricted opening protects a user from contacting previously stored used sharp medical instruments.

In a preferred embodiment the container has a body provided with longitudinal walls and laterally extending walls, a top panel and a bottom panel defining with the longitudinal and lateral walls the interior space for receipt of the new or used sharp medical instruments. With such a construction, the top panel includes first and second flaps and the flaps together define an entrance into the interior space of the container and through which medical instruments are removed from the body or are introduced, after use, into the interior space of the container. The longitudinal edge portion of one flap overlies the edge portion of the other flap when the entrance is restricted.

In a preferred embodiment the end edges of the first flap of the container are each provided with a closure tab. Each end wall is provided with a closure element mounted thereon which is cooperable with the corresponding closure tab for restricting the entrance opening and maintaining the flaps in a generally closed or restricted position.

A feature of the present invention is to provide a container of the aforementioned type wherein each end wall is provided with inner and outer surfaces, with each closure element being located on the outer surface and each corresponding closure tab being engagable with the outer surface of the corresponding end wall when the tab is engaged with the closure element to close or restrict the entrance to the container.

In an alternate embodiment of the invention, each closure element is located on the inner surface of the end wall and each corresponding closure tab is opposite the inner surface of the corresponding end wall when the tab is engaged with the closure element to close or to restrict the entrance.

Another feature of the present invention is to provide a container of the aforementioned type wherein each closure tab is of L-shaped configuration and each closure element is in the form of a twist type resilient element which is engagable around the L-shape closure tab to close or to restrict the entrance to the container.

Still another feature of the present invention is to provide a container of the aforementioned type wherein a closure element is pivotedly mounted on each end wall of the container and has an opening therein engagable with the L-shape closure tab for closing or restricting the entrance and maintaining the flaps in a generally closed position.

Finally, it is another feature of the present invention to provide a container which is provided with an elongated removable latching slide element which is designed to extend through aligned openings provided in the end extension walls of the container, with the slide extending across the upper flaps and cooperate therewith for maintaining the flaps and the entrance in a restricted or closed position.

It should be appreciated that a shipping container may be sold with the disposable container disclosed herein. In this way, both a container for shipment of the sharp medical instruments and the container for the disposal of the used sharp medical instruments are associated with each other in the same package.

Non-medical items may also be utilized with the container of the present invention. As an example, industrial items, chemical items, cosmetics and computer software may be transported in the container and after its useful life may be disposed of in the same container. When the container of the present invention is used with medical or chemical products, the container may contain an absorbent pad and/or chemical agents for neutralizing or cleaning the items.

These and other features of the present invention can be best understood from the following specification and drawings, of which the following is a brief description.

DETAILED DESCRIPTION OF A PREFERRED EMBODIMENT

Figure 1:
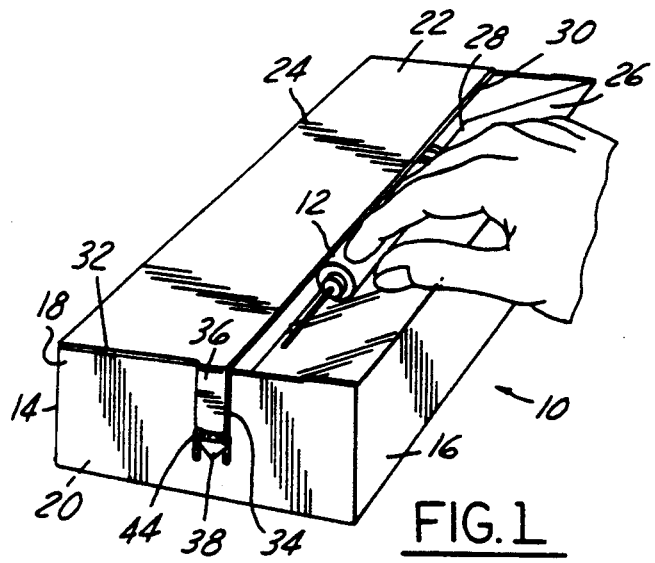
FIG. 1 is a perspective view of one embodiment of the present invention showing the top flaps in a closed or restricted position and defining a restricted opening through which a soiled or used sharp medical instrument may be inserted into the interior space of the container for disposal.
Figure 2:
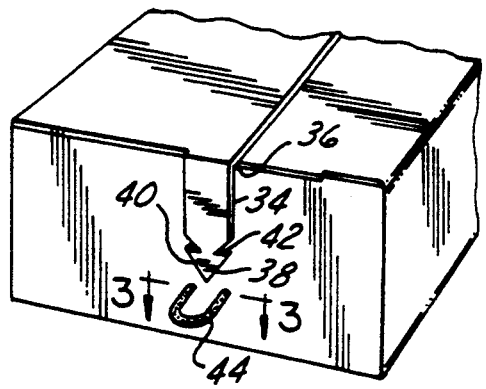
FIG. 2 is an enlarged fragmentary perspective view, with portions removed, showing the construction of the closure element and the closure tab which together holds the flaps in a closed or restricted position.
Figure 3:
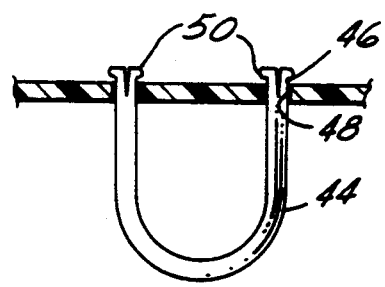
FIG. 3 is a sectional view taken along line 3—3 of FIG. 2 and showing the manner in which the U-shape closure element is attached to the end wall of the container.

Referring now to the drawings and in particular to FIGS. 1-3 inclusive, there is shown a container 10 which is optionally useable for both transport and/or disposal of medical instruments 12 as is illustrated and described herein. The container 10 includes a unitary body 14 made from a plastic material, with the body 14 having a pair of longitudinal walls 16 and a pair of lateral or end walls 18. The body 14 includes a bottom panel 20 and a top panel 22. The walls and panels just described defines an interior space for receipt of new or used sharp medical instruments. The body 14 is of generally rectangular configuration as shown in the drawings.

The top panel 22 includes a first flap 24 and a second flat 26. Each flap 24, 26 is integrally attached along one edge thereof by a living hinge to the corresponding longitudinal wall 16 whereby the container 10, when initially used, may have the flaps 24, 26 open to define a relatively large opening to permit the insertion of new sharp medical instruments into the interior of the body 14. The flaps 24, 26 may then be sealed by suitable adhesive tape or by other suitable fastening means in order to close the container and to transport the new medical instruments within the container body 14 to a hospital, clinic or doctors office for use. When the sharp medical instruments are required, the container 10 is opened, with the first and second flaps 24 and 26 of the top panel being moved about the corresponding living hinge along one longitudinal edge of the body 14 to open same and permit the removal of the new sharp medical instruments. Once the medical instruments have been removed, the medical personnel then adjusts the container 10 so that it thereafter can only be used to handle or to transport soiled sharp medical instruments. When the flaps 24, 26 are in a closed or restricted position, the first flap 24 overlies a longitudinal portion of the second flap 26, thus normally closing or restricting the entrance as is shown in FIG. 1. The first flap 24 and the second flap 26 are each provided with a pair of longitudinal edges and a pair of lateral edges. One longitudinal edge of each flap forms the living hinge with the corresponding longitudinal wall 16. The longitudinal edge 28 of the second flap 26 extends beneath the longitudinal edge 30 of the first flap 24 when the flaps are in a closed or restricted position.

Each end edge 32 of the first flap 24 is provided with a closure tab 34. The closure tab 34 is integrally connected to the first flap 24 by a living hinge 36. The opposite end of the closure tab 34 is provided with an arrow head 38 having a pair of downwardly converging tapered surfaces 40. The head 38 is provided with a pair of retaining abutment surfaces 42. Each end wall 18 is provided with a U-shape hook or closure element 44. Closure element 44 have ends 46 which extends through corresponding openings 48 provided in the end wall 18. The ends 50 of the closure tab or element 44 are enlarged so as to retain the closure element 44 on the end wall 18 as is shown in FIG. 3. The closure element 44 may be made from plastic material separate from the body 14. Other types of material may be used for the closure elements 44 such as metal or rubber.

In use after the sharp medical instruments, if any, have been removed from the body 14, each closure tab 34 is bent about the corresponding living hinge 36 so that the arrow head 38 points downwardly. Thereafter, the arrow head 38 extends through the closure element 44 until the abutments 42 engage the closure element 44 to lock or to retain the flaps 24 and 26 in a restricted or closed position. With such a construction a used sharp medical instrument 12 such as a hypodermic needle is insertable through the restricted opening of the container (FIG. 1) by applying a force to the pivotable second flap 26 to slightly enlarge the opening and permit the instrument 12 to be inserted into the interior of the body 14. Once the container 10 has been filled with one or more soiled sharp instruments 12 it can be safely disposed of according to acceptable hygienic and environmental rules and regulations.

Figure 4:
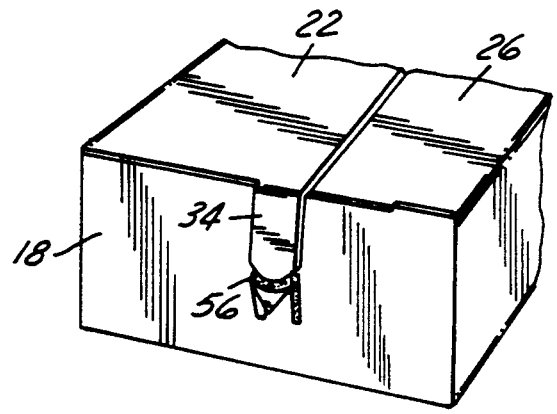
FIG. 4 is an enlarged fragmentary perspective view of another embodiment of the container.

FIG. 4 is similar to FIGS. 1-3 inclusive with the exception that the closure element 56 is in the form of a resilient member such as a rubber band which has the ends thereof fixed by adhesive or other suitable means to the end wall 18. When the top flaps 24 and 26 are closed, the closure tab 34 having one or more abutment surfaces 42 is inserted through the resilient closure element 56 whereby the element 56 engages the abutment 42 to retain the flaps 24, 26 in a generally closed position but capable of defining a restricted opening as in FIG. 1.

Figure 5:
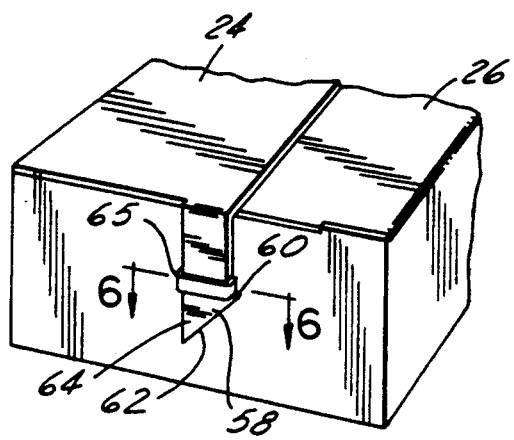
FIG. 5 is an enlarged fragmentary perspective view of still another embodiment of the container.
Figure 6:
FIG. 6 is a sectional view taken along line 6—6 of FIG. 5 and showing the manner in which the closure tab is permanently engaged with the closure element.

FIG. 5 is a further embodiment of the present invention wherein the first flap 24 is provided with a closure tab 58 having only one abutment surface 60 and one sloping edge 62. The other edge 64 constitutes a continuation of the corresponding edge of the tab 58. The closure element 65 is integrally formed with the corresponding end wall 18 during the manufacture of the plastic body 20. The closure element 65 is elongated, is of generally rectangular configuration and has an opening 66 provided therein as shown in FIG. 6. When the flaps 24 and 26 are closed, the closure element 58 extends through the opening 66, with the abutment surface 60 engageable with the bottom surface 68 of the closure element 65 as best illustrated in FIGS. 5 and 6. With such a construction, the flaps 24 and 26 permit or define a restricted opening whereby used soiled sharp medical instruments may be placed within the interior of the container body 14 for disposable according to environmental and hospital standards.

Figure 7:
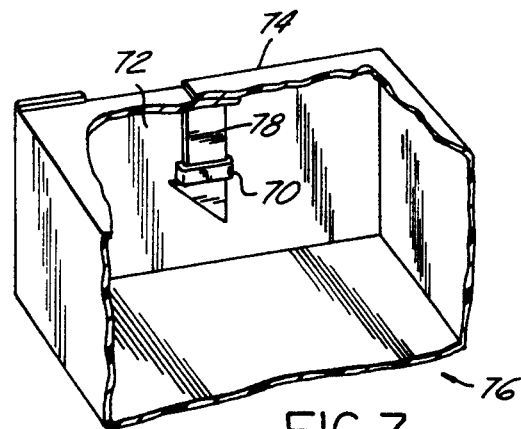
FIG. 7 is a fragmentary perspective view, with portions broken away, showing another embodiment of the present invention, with the closure element and closure tab mounted within the interior of the container when the flaps are in a restricted or closed position.

Another embodiment of the present invention is illustrated in FIG. 7 wherein the hollow closure element 70 is of generally rectangular configuration and is located on the inner surface 72 of the end wall 74 of the container body 76. The closure element 70 and the closure tab 78 are of similar construction to the corresponding elements identified and described in connection with FIGS. 5 and 6. The major differences are that the closure tab 78 and the closure element 70 are located within the interior of the container 76 rather than on the outside of the container.

Figure 8:
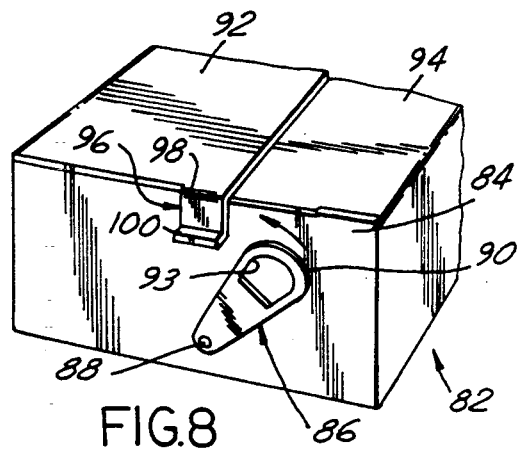
FIG. 8 is a fragmentary perspective view of still another embodiment of the present invention, with the closure tab on each end wall being pivotable and engagable with an L-shape closure element provided on the end of one of the flaps of the top panel.
Figure 9:
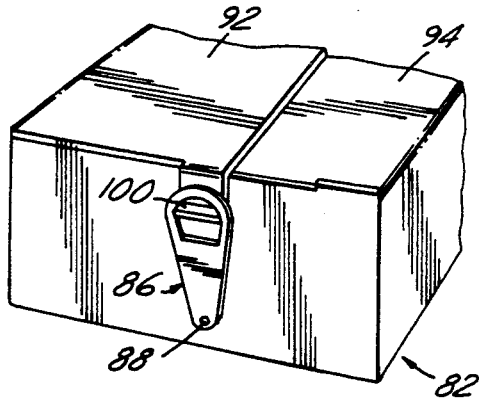
FIG. 9 is a fragmentary perspective view similar to FIG. 8 but showing the pivotable locking or closure element in engagement with the L-shape closure tab.

FIG. 8 shows another embodiment wherein the container body 82 has on each end wall 84 thereof a pivotable closure element 86. This element 86 is pivoted at one end by a suitable rivet at 88. The opposite end 90 is provided with a window or opening 92. The container body 82 is similar in construction to the other bodies previously described with the exception that the first flap 92 which cooperates with the second flap 94 in generally the same manner as previously described is provided with a closure tab 96 of L-shape configuration. This closure tab 96 includes a vertical portion 98 and a 90 degrees bent portion 100. After the removal of the new medical instruments, if any, the container 82 is readied for use as a disposal container. The pivotable closure element 86 is pivoted about pivot point or rivet 88 so as to move the closure element 86 to the left as viewed in FIG. 8 whereby the opening 92 of the closure element 86 engages the L-shape element or bent portion 100 as best illustrated in FIG. 9.

Figure 10:
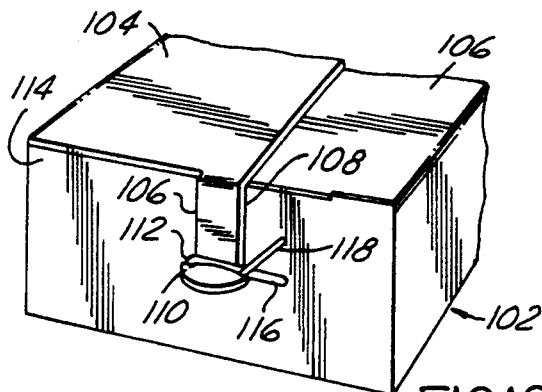
FIG. 10 is a fragmentary perspective view of still another embodiment of the container, with the closure tab being of L-shaped configuration and the closure element being a resilient twistable type member carried by the end wall and tied over the closure tab to secure the flaps in a restricted position.

FIG. 10 illustrates another embodiment of the container which is useable to transport soiled sharp medical instruments. The container 102 is constructed as the other embodiments previously described with the exception of the first flap 104 which cooperates with the second flap 106 to define the restricted opening as described previously. The first flap 104 has an L-shape closure element 106. Element 106 includes a vertical portion 108 and an angularly related catch or leg portion 110. The catch portion 110 forms a head having an abutment surface 112 directly opposite the corresponding end wall 114. Each end wall 114 of the container 102 has a pair of holes whereby a twist type locking element 116 may be inserted from the inside of the container 102 to the outside thereof. The twist like element or tie 116 is the type of element used on a garbage bag to close it. The element 116 may be suitably affixed by adhesive to the inside surface of the end wall 114, with the ends of the closure element 116 extending through the end wall 114 to the exterior thereof. Once the flaps 104 and 106 are as shown in FIG. 7 the ends 118 of the elements are twisted around the enlarged head 110 against the abutment surface 112 to retain the top flaps 24, 26 of the container 102 in a closed position. With such a construction, the flaps 104 and 106 are cooperable to define a restricted opening of the type described previously to permit the insertion of a soiled sharp medical instrument.

Figure 11:
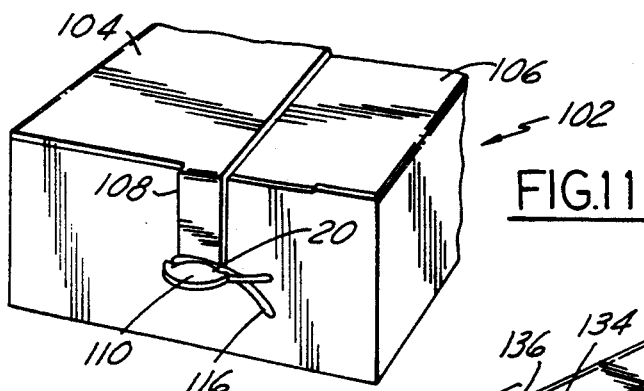
FIG. 11 is a fragmentary perspective view of still another embodiment of the present invention similar to FIG. 10.

FIG. 11 is a view of a modified container, similar in many respects to the embodiment of FIG. 10, with the exception that the head 110 provided on the locking element 106 and the corresponding abutment surface 120 and the tie or element 116 is looped around and have the ends tied in place to affix the flaps 104 and 106 in a disposal condition ready to accept used soiled sharp medical instruments as described previously.

Figure 12:
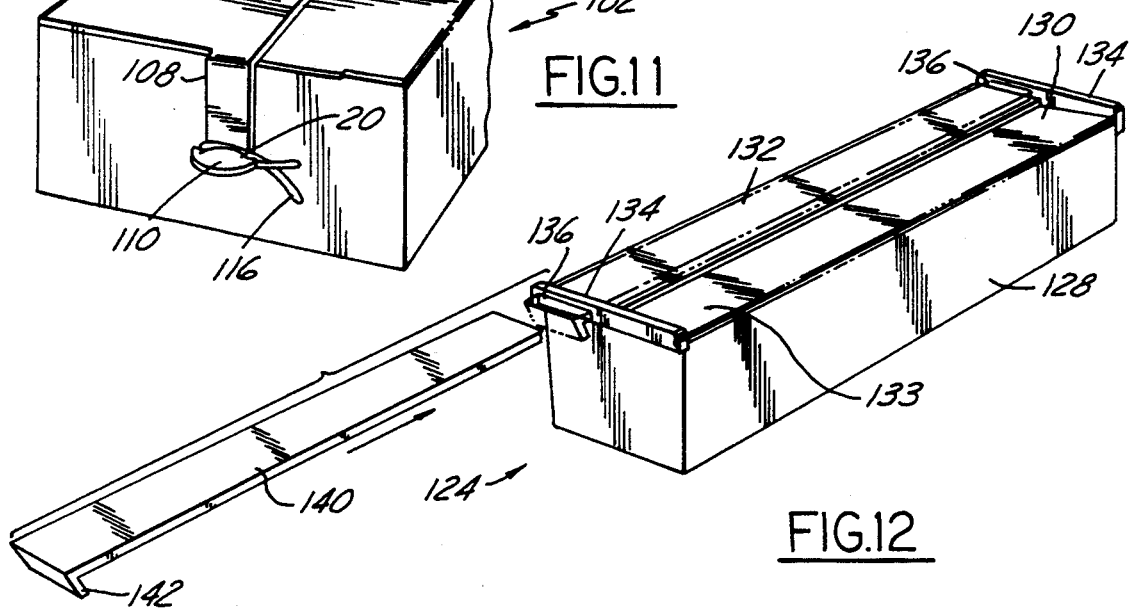
FIG. 12 is a perspective view of the final embodiment of the present invention showing the use of an elongated removable latching slide element to maintain the top cover flaps of the container in a closed or restricted position.

FIG. 12 shows another container 124 having a pair of end walls 126, a pair of longitudinal walls 128, a bottom panel, not shown, and a top panel 130 consisting of a first flap 132 hinged at one edge along one longitudinal edge of the wall 128 and a second flap 133 hinged along the upper longitudinal edge of the wall 128. The end walls 126 are each provided with an extension wall 134. Each extension wall 134 has a slot 136 aligned with the slot 136 in the opposite extension wall 134. An elongated removable latching slide element 140 having a downwardly turned leg 142 is provided. When the first and second flaps 132, 133 are in a closed or restricted position, the element 140 is insertable through the aligned openings 136 of the end extension walls 134 to lock the first flap 132 in place. With such a construction, the second flap 133 has a portion which is located underneath the locked in first flap 132. Thus, in use, when a used sharp medical instrument is to be placed within the interior of the container 124, the second flap 133 is depressed and the used medical instrument inserted into the interior of the container 126 in the manner previously described as mentioned previously.

According to the present invention, a container having a unitary plastic body may be provided with a plurality of selectively utilizable openings. A first relatively large opening may be provided to permit the insertion into the container and the removal from the container of new sharp medical instruments. After the medical instruments, if any, have been removed from the container, a second relatively restricted opening may then be provided for the receipt of the soiled sharp medical instruments, such as is shown in FIG. 1. The new medical instruments may initially be stored in the container. The container is transported in a closed condition without the closure tabs and closure elements being engaged. Once the container with the new medical instruments have been transported and when conditions require, they are removed from the container. Thereafter, the medical attendant reconfigures the container into a structure such that the closure tabs and closure elements provided on the end wall of the container are engaged so as to define only a restricted opening between the first and second flaps of the top panel of the container. At such time, used sharp medical instruments may be inserted into the container through the restricted opening and thereafter the container is disposed of according to hospital and environmental safety standards.

It should be understood that the container may be taken to a location where the used sharp medical instruments may be sterilized and reused according to environmental, hospital and safety standards. As an example, a person could cut the tabs and remove the used medical instruments for sterilization and thereafter dispose of the used container.

The various prior art patents include containers designed to decontaminate or neutralize used sharp medical instruments. The present invention is useful not only with sharp medical instruments but with other types of medical instruments that may require disposal according to safety and environmental conditions.

Preferred embodiments of this invention have been disclosed. However, a person of ordinary skill in the art would recognize that certain modifications would come within the scope of this invention. For that reason, the following claims should be carefully examined in order to determine the true scope and content of this invention.

I claim the following:

1. A container for use with medical instruments comprising:
   a body having longitudinal walls and lateral walls, a top panel and a bottom panel defining with said longitudinal and lateral walls an interior space for receipt of medical instruments;
   said top panel including first and second flaps, and an entrance to said interior space defined between said flaps and through which the medical instruments are introduced to said interior space;
   said flaps when in a closed position having said first flap overlying a longitudinal portion of said second flap thus normally closing said entrance;
   said first and second flaps of said top panel each having a pair of longitudinal edges and a pair of lateral edges;
   said first and second flaps of said top panel each being integrally connected by a living hinge along one longitudinal edge thereof to one of the longitudinal walls of said body;
   the other longitudinal edge on said first flap overlying said second flap when said entrance is closed;
   the end edges of said first flap each being provided with a closure tab, said closure tab having opposed planar faces and opposed side edges and an arrow head with abutments on the side edges for engagement with a corresponding closure element mounted on each lateral wall, each closure element having structure cooperable to engage the abutments for closing the entrance and maintaining said flap in a closed position.

2. The container as recited in claim 1, wherein each lateral wall has inner and outer surfaces, with each closure element located on the outer surface and each corresponding closure tab engageable with the outer surface of the corresponding lateral wall when engaged with the closure element to close the entrance.

3. The container as recited in claim 1, wherein each closure tab has a plurality of abutments for engaging the corresponding closure element at different locations thereon.

4. The container as recited in claim 1, wherein each closure element is of U-shaped configuration having the legs thereof fixed to the corresponding end wall.

5. The container as recited in claim 1, wherein each closure tab and each closure element are located on the exterior of the corresponding lateral wall.

6. The container as recited in claim 1, wherein each closure tab has a living hinge connection to the end edge of said first flap.

7. The container as recited in claim 1, wherein each closure element is integrally formed with the corresponding lateral wall, said closure element extending outwardly from the lateral wall.

8. The container as recited in claim 7, wherein said closure tab is located exteriorly of the body.

9. A container for use with medical instruments comprising:
   a body having longitudinal walls and lateral walls, a top panel and a bottom panel defining with said longitudinal and lateral walls an interior space for receipt of medical instruments;
   said top panel including first and second flaps, and an entrance to said interior space defined between said flaps and through which the medical instruments are introduced to said interior space;
   said flaps when in a closed position having said first flap overlying a longitudinal portion of said second flap thus normally closing said entrance;
   said first and second flaps of said top panel each having a pair of longitudinal edges and a pair of lateral edges;
   said first and second flaps of said top panel each being integrally connected by a living hinge along one longitudinal edge thereof to one of the longitudinal walls of said body;
   the other longitudinal edge on said first flap overlying said second flap when said entrance is closed;
   the end edges of said first flap each being provided with a closure tab, said closure tab having opposed planar faces and opposed side edges and an arrow head with one abutment on the side edges for engagement with a corresponding closure element mounted on each lateral wall, each closure element having structure cooperable to engage the abutment for closing the entrance and maintaining said flap in a closed position.

* * * * *